US007972592B2

(12) United States Patent
Hyöty et al.

(10) Patent No.: US 7,972,592 B2
(45) Date of Patent: Jul. 5, 2011

(54) PREVENTION OF TYPE 1 DIABETES AND OTHER NON-POLIO ENTEROVIRUS DISEASES

(76) Inventors: Heikki Hyöty, Tampere (FI); Mikael Knip, Tampere (FI)

( * ) Notice: Subject to any disclaimer, the term of this patent is extended or adjusted under 35 U.S.C. 154(b) by 0 days.

(21) Appl. No.: 11/471,937

(22) Filed: Jun. 21, 2006

(65) Prior Publication Data

US 2006/0240466 A1    Oct. 26, 2006

Related U.S. Application Data

(62) Division of application No. 10/009,016, filed as application No. PCT/FI00/00220 on Mar. 17, 2000, now Pat. No. 7,090,855.

(60) Provisional application No. 60/140,872, filed on Jun. 24, 1999.

(51) Int. Cl.
    *A61K 35/00* (2006.01)
    *A61K 48/00* (2006.01)
(52) U.S. Cl. .................................. 424/93.1; 424/217.1
(58) Field of Classification Search .................. None
    See application file for complete search history.

(56) References Cited

U.S. PATENT DOCUMENTS 5,723,283 A    3/1998  Classen .............................. 435/4

OTHER PUBLICATIONS

Roivaninen et al. J. Clin. Endocrinol, 2000, vol. 85. No. 1. pp. 432-440.*
Fohlman Scand. J. Infect. Dis. Suppl. 1993; vol. 88, pp. 103-108.*
See et al. Scand. J. Infect. Dis. Suppl. 1994;26 (6):739-747.*
Huber et al. Virus Immunity 2004, vol. 17, No. 3, pp. 358-369.*
Klump et al. J. Virol. 1990, vol. 64, No. 4, pp. 1573-1583.*
Jeong et al. Microbiol. Immunol. 2007, vol. 51(11), pp. 1091-1098.*
Melliins et al. J. Exp. Med.1988, vol. 168, pp. 1531-1537.*
Diabetes Holisticonline.com published on line 1998-2007 ICBS. Inc., pp. 1-3.*
Hyoty et al. Clinical and Diagnostic Virology 1998, vol. 9, pp. 77-84.*
Mertens et al. Euro. J. Pediatr. 1983, vol. 140, pp. 293-294.*
Screening of organ donors for anti-islets antibodies and characterization of pancreatic histology in an antibody positive subject. Giannani, Dotta, Di Mario, Scipioni, Grassetti, Liggins, Yu, Eisenbarth. Immunology of Diabetes Society Conference. Cambridge England Mar. 28-31, 2004.
Human Beta-Cell Specific Enteroviral Infection Impairs insulin secretion and upregulates islet chemokine and fas expresson. Grassetti, Scipioni, Del Guerra, Lettieri, Sbrana, Mario, Marchetti, Dotta. Immunology of diabetes society conference. Cambridge England Mar. 28-31, 2004.
Demonstration of enterovirus infection in islets of two patients with type I diabetes. Dotta, Santangelo, Marselli, Dionisi, Scipioni, Masini, van Halteren, Del Prato, Di Mario, Roep, Marchetti. Diabetes/Metabolism Research and Reviews. Nov.-Dec. 2002.
Enterovirus infection in human pancreatic islet cells, islet tropism in vivo and receptor involvement in cultured islet beta cells. Ylipaasto, Klingel, Lindberg, Otonkoski, Kandolf, Hovi, Riovainen. Diabetologia (2004).
Virus-induced diabetes mellitus. Yoon, Austin, Onodera, Notkins. vol. 300 No. 21 Laboratory of Oral Medicine, 1997.
Human beta cell specific enteroviral infection induces pro-apoptotic changes as evidenced by microarray gene expression profiling. Grassetti, Scipioni, Lupi, Del Prato, Marchetti, Dotta. Diabetologia vol. 47 , article 488 p. A179, 2004.
Enterovirus-related type 1 diabetes melliltus and antibodies to glutamic acid decarboxylase in Japan. Kawashima, Ihara, Loi, Oana, Sato, Kato, Takami, Kashiwagi, Takekuma, Hoshika, Mori. Journal of Infection, Aug. 2004 49(2): 147-51.
Simultaneous Onset of Type 1 Diabetes Mellitus in Identical Infant Twins with Enterovirus Infection. Smith, Clements, Riding, Collins, Bottazzo, Taylor. Diabetic Medicine 1998 15: 515-517.
Enterovirus RNA is found in Peripheral Blood Mononuclear Cells in a Majority of Type 1 Diabetic Children at Onset. Yin, Berg, Tuvemo, Frisk. Diabetes, vol. 51, Jun. 2002.
Reduced Frequency of HLA DRB1*03-DQB1*02 in Children with Type 1 Diabetes Associated with Enterovirus RNA. Craig, Howard, Silink, Rawlinson. Journal of Infectious Diseases May 15, 2003.
Enterovirus Variants in the serum of children at the onset of Type 1 diabetes mellitus. Nairn, Galbraith, Taylor, Clements. British Diabetic Association, Diabetic Medicine 16, 509-513 1999.
Coxsackie B Virus infection and onset of childhood diabetes. Clements, Galbraith, Taylor. The Lancet, vol. 346, Jul. 22, 1995 pp. 221-223.
Detection of Coxsackie B Virus RNA Sequences in Whole Blood Samples from adult patients at the onset not Type 1 diabetes melliltus. Andreoletti, Hober, Hober-Vandenberghe, Belaich, Vantyghem, Lefebvre, Wattre,. Juornal of Medical Vriology 52:121-127 (1997).
Neonatal Type 1 diabetes associated with maternal echovirus 6 infection: a case report. Otonkoski, Roivainen, Vaarala, Dinesen, Leipala, Hovi, Knip. Diabetologia (2000) 43: 1235-1238.
Serologic Evidence of an Association between Enteroviruses and the onset of Type 1 diabetes mellitus. Helfand, Gary, Jr., Freeman, Anderson, Pallansch. The Journal of Infectious Diseases 1995: 172-1206-11.
Increased level of interferon-α, in blood of patients with insulin-dependent diabetes mellitus: Relationship with coxsackievirus B infection. Chehadeh, Weill, Vantyghem, Alm, Lefebvre, Wattre, Hober. The Journal of Infectious Diseases 2000; 181:1929-39.
Characterization of the T-Cell response to Coxsackievirus B4. Evidence that effector memory cells predominate in patients with Type 1 diabetes. Varela-Calvino, Ellis, Sgarbi, Dayan, Peakman. Diabetes, vol. 51, Jun. 2002.

(Continued)

Primary Examiner — Bao Li
(74) Attorney, Agent, or Firm — Ladas & Parry LLP (57) ABSTRACT

Live virus vaccines comprise attenuated viruses, while other vaccines comprise killed viruses or parts thereof. It has now been found that the immune response induced by oral poliovirus vaccine (OPV), which is a live vaccine, is cross-reactive with non-polio enteroviruses. OPV is therefore useful in the prevention of non-polio enterovirus diseases, especially Type 1 diabetes mellitus (IDDM). OPV is also useful in combination with killed/subunit non-polio enterovirus vaccines, whereby it prevents harmful side-effects of the killed/subunit vaccine by shifting the immune response from a harmful Th2-type response to a Th1 type response.

10 Claims, 1 Drawing Sheet

OTHER PUBLICATIONS

Prediction and prevention of Type 1 diabetes mellitus. PS. 30,. Schlosser, Mentel Moya-Suri, Wassmuth, Gurtler, Moritz, Greifswald, Arndt. Diabetologia, vol. 47 supplement 1, A 183, 2004.

Enterovirus infections are associated with the induction of β-Cell autoimmunity in a prospective birth cohort study. Salminen, Sadeharju, Lonnrot, Vahasalo, Kupila, Korhonen, Ilonen, Simell, Knip, Hyoty. Journal of Medical Virology 69:91-98 (2003).

Enterovirus infections as a risk factor for type I diabetes: virus analyses in a dietary intervention trial. Sadehauju, Hamalainen, Knip, Lonnrot, Koskela, Virtanen, Ilonen, Akerblom, Hyoty. Clin. Exp. Immunol 2003; 132: 271-277.

Enterovirus antibody levels during the first two years of life in prediabetic autoantibody-positive children. Sadeharju, Lonnrot, Kimpinaki, Savola, Erkkila, Kalliokoski, Savolainen, koskela, Ilonen, Simell, Knip, Hyoty. Diabetologia (2001) 44:.818-823.

Enterovirus RNA in Serum is a risk factor for beta-cell automimmunity and clinical Type 1 diabetes: A prospective study. Lonnrot, Salminen, Knip, Savola, Kulmala, Leinikki, Hyypia, Akerblom, Hyoty. Juornal of Medical Virology 61:214-220 (2000).

T-Cell responses to enterovirus antigens in children with Type 1 diabetes. Juhela, Hyoty; Roivainen, Harkonen, Putto-Laurila, Simell, Ilonen. Diabetes, vol. 49, Aug. 2000 pp. 1308-1313.

Islet cell antibody seroconversion in children is temporally associated with enterovirus infections. Hiltunen, Hyoty, Knip, Ilonen, Reijonen, Vahasalo, Riovainen, Lonnrot, Leinikki, Hovi, Akerblom. The Journal of Infectious Diseases 1997; 175:554-60.

A prospective study of the role of coxsackie B and other enterovirus infections in the pathogenesis of IDDM. Hyoty, Hitunen, Knip, Laakkonen, Vahasalo, Karjalainen, Koskela, Roivainen, Leinikki, Hovi, Akerblom. Diabetes, vol. 44 Jun. 1995 pp. 652-657.

Detection of enterovirus RNA sequences in serum samples form autoantibody-positive subjects at risk for diabetes. Coutant, Palmer, Carel, Cantero-Aguilar, Lebon, Bougneres. 2002 Diabetes UK Diabetic Medicine, 19 966-971.

Echovirus 4 and Type 1 diabetes mellitus. Diaz-Horta, Bello, Cabrera-Rode, Suarez, mas, Garcia, Abalos, Jofra, Molina, Diaz-Diaz, Di Mario. Autoimmunity vol. 34 pp. 275-281, 2001.

Type 1 diabetes islet associated antibodies in subjects infected by echovirus 16. Cabrera-Rode, Sarmiento, Tiberti, Molina, Barrios, Hernandez, Diaz-Horta, Di Mario. Diabetologia (2003) 46: 1348-1353.

Hiltunen M etal: "Immuniological and Type 1 Diabetes Mellitus" Durg Safety; vol. 20, No. 3; 1999; pp. 207-212.

Fohlman J et al: "Vaccination of BALB/C Mice Against Enteroviral Mediated Miocarditis"; Vaccine; vol. 8, Aug. 1990; pp. 381-384.

Database Dialog Inf. Serv. Medline [Online] Clements G B et al; "Coxackie B Virus Infection and Onset . . . Commnets"; Retrieve . . . Medicine; File 155, Accesion No. 08341526.

Juhela S et al: "Enterovirus Infections and Enterovirus Specific T-Cell Responses in Infancy"; J.Med. Virology; vol. 54; 1998; pp. 226-232.

EPI News: Coverage of the Childhood Vaccination Programme, 1998-2001 (2002) No. 15.

Fohlman, et al. Scand. J. Infect. Dis.—Supple. 88: 103-108 (1993).

Hviid, et al. (New England Journal of Medicine 350 (2004) (14) 1398-1404.

Graves, et al. (Diabetes Care) (1999) (22) 1694-1699.

Harjulehto-Mervaala, et al. (Clinical Infectious Diseases—Abstract Only) 18(3) (1994) 414-420.

WHO Weekly Epidemiological Record (1996) 71, 133-140.

Viskari, et al. (Journal of Medical Virology) (2004) 72, 610-617.

M. Hiltunen, et al, "Immunisation and Type 1 Diabetes Melitus", *Drug Safety*, (1999), vol. 20, No. 3, pp. 207-212.

S. Juhela, et al; "Enterovirus Infections and Enterovirus Specific T-Cell Responses in Infancy", *J. Med. Virology* (1998), vol. 54, pp. 226-232.

R.K. Zimmerman, et al; "Poliovirus Vaccine Options", *American Family Physician*, (1999), vol. 59, No. 1, pp. 113-118.

Canadian Office Action in Application No. 2,376,923 Issued Dec. 17, 2010.

Zhang, et al. Coxsackievirus B3-Induced Myocarditis, American Journal of Pathology, vol. 150, No. 6, Jun. 1997.

* cited by examiner

Figure 1

PREVENTION OF TYPE 1 DIABETES AND OTHER NON-POLIO ENTEROVIRUS DISEASES

This application is a divisional application Ser. No. 10/009, 016 filed on Mar. 12, 2002, now U.S. Pat. No. 7,090,855 which is a 371 of PCT/FI2000/00220 filed Mar. 17, 2000, which designated the U.S., claims the benefit thereof and incorporates the same by reference. The nonprovisional application designated above, namely application PCT/FI2000/00220, filed Mar. 17, 2000, claims the benefit of U.S. Provisional Application No. 60/140,872 filed Jun. 24, 1999.

FIELD OF THE INVENTION

The invention relates to the prevention of Type 1 diabetes and other non-polio enterovirus diseases by a novel vaccination regime based on extensive immunisations by currently available oral poliovirus vaccine (OPV) and/or by new non-polio enterovirus vaccines.

The invention provides prevention of Type 1 diabetes mellitus (IDDM) and other non-polio enterovirus diseases by eliminating the risk effect of enterovirus infections. This is achieved by a novel immunisation regime, which is based on the induction of systemic and local mucosal Th1-type T-cell immunity by oral poliovirus vaccinations and optionally induction of Th2-type humoral immunity by a new enterovirus vaccine which induces neutralizing antibodies against appropriate enterovirus serotypes. These two regimes can be used separately or in combination.

More precisely the present invention relates to the use of oral poliovirus vaccine (OPV) for the manufacture of a vaccine against non-polio enterovirus diseases, and especially against Type 1 diabetes mellitus (IDDM). When OPV is used together with a vaccine, which induces serotype specific immunity against non-polio enteroviruses, harmful side effects of the non-polio enterovirus vaccine can be avoided. The invention thus provides a vaccine composition comprising said two vaccines.

BACKGROUND

Enterovirus infections are usually subclinical but cause also various kind of diseases. Typical enterovirus diseases are meningitis, paralysis, myocarditis, generalized infections in newborns, hand, foot and mouth-disease, herpangina, pleurodynia, hepatitis, rash, exanthemas and respiratory diseases including pneumonia. In addition, enterovirus infections have been suspected to play a role in the pathogenesis of dilated cardiomyopathy, atherosclerosis, postviral fatique syndrome and Type 1 diabetes mellitus.

The group of enteroviruses includes a total of 64 different serotypes. Polioviruses are the most widely known enteroviruses including 3 different serotypes (poliovirus types 1, 2 and 3) which all can cause meningitis and typical paralytic poliomyelitis (flaccid paralysis). Meningitis is frequently caused by several non-polio enteroviruses, which are the most common cause of aseptic meningitis. Myocarditis is caused mainly by coxsackie B serotypes but also other enterovirus serotypes may be involved. Hand, foot and mouth-disease is mainly caused by certain coxsackie A serotypes and severe infections of infants are related to coxsackie B serotypes. Paralytic diseases can also be caused by some other serotypes than poliovirus serotypes. The serotypes related to atherosclerosis and Type 1 diabetes are not known. In type 1 diabetes the most suspected ones have been coxsackieviruses B4 and B5 but also other than coxsackie B serotypes may be involved.

The only enterovirus vaccine, which has been used in human beings is poliovirus vaccine. This vaccine includes all three poliovirus serotypes and gives effective prevention against paralytic poliomyelitis. The protection is based on the induction of neutralizing antibodies, against these serotypes and is serotype specific. Thus, neutralizing antibodies, which are induced by poliovirus vaccines do not protect against any other enterovirus serotypes than the three poliovirus serotypes. The role of T-cell mediated immune responses in the protection against poliovirus infections is not known. The generally accepted view is that they play only a minor role while antibodies are more important in the elimination of infection and in the protection against reinfections.

Two different types of poliovirus vaccine have been developed. The killed inactivated poliovirus vaccine (IPV; Salk vaccine) includes formalin-inactivated polioviruses (all 3 serotypes). This vaccine is given parenterally using subcutaneous injections. It induces a Th2-type immune response characterized by strong antibody response and high levels of neutralizing antibodies against all poliovirus serotypes and gives effective prevention against paralytic poliomyelitis. However, it induces only weak local immune response in the gut. As gut associated lymphoid tissue is the primary replication site of polioviruses, IPV vaccine can not protect against poliovirus infection but only against the complications of infections. IPV can induce only weak cytotoxic T-cell immune responses.

The other poliovirus vaccine is oral poliovirus vaccine (OPV; Sabin vaccine) which includes live attenuated polioviruses (all three serotypes). This vaccine is given per os and the virus replicates in the same way as the wild polioviruses in the body. As the vaccine is given per os in the same way as natural enterovirus infections are acquired, it induces strong local immunity in the intestine, which prevents from later poliovirus infections. Thus, OPV vaccinated individuals usually do not become infected by polioviruses because the virus is not able to replicate in the intestine. The nature of this protection is not completely understood but it probably depends on both neutralizing antibodies and T-cell mediated immunity. OPV induces stronger T-cell responses than IPV and it induces mainly Th1-type T-cell responses characterized by strong cytotoxic T-cell responses.

Vaccines against non-polio enteroviruses are not available for human use. The reason is that the large number of enterovirus serotypes makes it difficult to make a pan-enterovirus vaccine and, on the other hand, the serotypes, which are causing the most severe non-polio enterovirus diseases, are highly variable. Myocarditis and cardiomyopathies have been associated with coxsackie B group viruses, meningitis and neonatal infections with several different serotypes and practically nothing is known about the serotypes possibly related to the development of atherosclerosis. In Type 1 diabetes the responsible serotypes are not known except that polioviruses are not involved. The general view is that poliovirus vaccines should not be effective in the prevention of Type 1 diabetes or other non-polio enterovirus diseases, but that the prevention of non-polio enterovirus diseases would require new vaccines which should induce neutralizing antibodies against the serotypes to be protected. Another reason for the lack of human non-polio enterovirus vaccines is that the safety of such vaccines has not been reliably confirmed. Thus, there is no effective vaccine or any other treatment for the prevention of non-polio enterovirus diseases in man.

Inactivated and subunit vaccines which include certain coxsackie B viruses have been tested in animal models. They have induced good antibody levels in mice and rabbits and effectively protected from infections caused by the serotypes which were included in the vaccine (Fohlman et al., 1990 and 1993; See and Tilles, 1994 and 1997). However, these vaccines have not been tested in human beings. The main reason for this is that the current knowledge on the mechanisms of immune protection against enteroviruses is limited and the safety of such vaccines can not be guaranteed. The safety issue has become very important after the discovery of the unexpected side-effects related to the use of inactivated respiratory syncytial virus (RSV) and measles vaccines in humans (Fulginiti et al., 1967; Harris et al., 1969; Kapikian et al., 1969). These vaccines paradoxically increased the severity or modulated the course of natural infections. The most probable explanation for these adverse effects is that these kind of inactivated vaccines generally induce good antibody response but very poor cytotoxic T-cell response. Thus, they may have induced a shift towards Th2-type antibody mediated immunity which resulted in the atypical symptoms. This indicates the need for very detailed data on the effect of the vaccine on the course of natural infections and careful evaluation of the safety issues.

The advantage of the immunization regime of the present invention is that it is based on the oral poliovirus vaccine (OPV) which has been extensively used in almost all countries of the world and which has proved to be very safe and effective. The poliovirus vaccines are actually one of the most effective and safest vaccines ever developed and have led to an almost complete eradication of poliovirus infections from the world. The only clinically relevant complication of OPV is the risk of vaccine associated paralysis. However, its frequency is extremely low (about 1 per 1-10 milj. vaccinees).

The advantage of the immunisation regime of the present invention is that it is based on the oral poliovirus vaccine (OPV) which has been extensively used in almost all countries of the world and which has proved to be very safe and effective. The poliovirus vaccines are actually one of the most effective and safest vaccines ever developed and have led to an almost complete eradication of poliovirus infections from the world. The only clinically relevant complication of OPV is the risk of vaccine associated paralysis. However, its frequency is extremely low (about 1 per 1-10 milj. vaccinees).

The general view is that immunity against enterovirus infection is based on the presence of neutralizing antibodies against the virus. These antibodies can efficiently neutralize the virus when it enters the body. The significance of neutralizing antibodies is reflected by the fact that patients who have abnormally low levels of antibodies due to an immune deficiency are particularly susceptible for enterovirus infections. Neutralizing antibodies can be detected for prolonged periods after the infection. They contribute to the eradication of the virus during primary enterovirus infection and protect against reinfections. However, they can not protect against infections, which are caused by other serotypes. Thus, the protection by these antibodies is serotype specific. Accordingly, it is generally thought that it is essensial for the efficacy of enterovirus vaccines that the vaccine is able to induce high titres of neutralizing antibodies against the serotypes which should be protected. The only currently used enterovirus vaccine is poliovirus vaccine which includes all three poliovirus serotypes.

The present invention is based on the finding that, in contrast to the general paradigm, oral poliovirus vaccines could also protect against other enterovirus infections than poliovirus infections and could therefore be used for the prevention of various non-polio enterovirus diseases, which have been described in detail in previous paragraphs, and diseases where the role of enteroviruses has been suspected including Type 1 diabetes mellitus, chronic fatigue syndrome and atherosceloris. This protection would be based on efficient induction of T-cell responses and local mucosal immunity by repeated OPV vaccinations. T-cell immune responses are known to cross-react between certain enterovirus serotypes when analysed in vitro by T-cell proliferation assay (Beck and Tracy, 1990; Graham et al., 1993). However, it was not known whether this cross-reactivity had any biological significance in vivo. It was not either known to what extent T-cell responses which are induced by OPV vaccinations can cross-react with non-polio enteroviruses and whether this had any clinical relevance.

We have previously evaluated these questions by analysing enterovirus specific T-cell responses in young infants. We found that some infants, who had never experienced any coxsackievirus B infection according to the lack of neutralizing antibodies, had strong T-cell proliferation response against purified coxsackievirus B4 antigen, which probably reflects the cross-reactivity of T-cells which have initially been induced by other enterovirus infections (Juhela et al., 1998). In addition, polio vaccination at the age of 6 months induced stronger T-cell response to purified coxsackievirus B4 and poliovirus antigens in children who had serological evidence of previous enterovirus infection compared to children who had no previous enterovirus infections (Juhela et al., 1998). This suggests that T-cells can cross-react between polioviruses and non-polio enteroviruses.

Our aim is to utilise this T-cell cross-reactivity by priming cross-reactive T-cell memory using OPV vaccinations. This, in turn, would make the immune responses to other enteroviruses stronger and more rapid (secondary-type response) and in this way speed up the eradication of the virus during acute non-polio enterovirus infections. OPV can not totally protect from these infections as it does not induce neutralizing antibodies against non-polio enteroviruses but it may protect against viremia and severe illnesses by potentiating the T-cell responses by inducing cross-reactive memory T-cells. This kind of T-cell help can potentiate both the production of neutralizing antibodies during infection as well as cytotoxic T-cell responses against non-polio enteroviruses. It may also booster antibodies against other enteroviruses than the serotype causing the acute infection by eliciting anamnestic immune responses. Induction of anamnestic responses means that OPV stimulates memory T-cell clones, which have originated from previous enterovirus exposures and in this way leads to their activation and induction of antibodies against all these serotypes. This kind of anamnestic response is used in the present regime to enhance enterovirus antibody levels in pregnant women thus providing protection for their infants.

SUMMARY OF THE INVENTION

One object of the present invention is to provide a method of preventing non-polio enterovirus diseases, especially Type 1 diabetes (IDDM).

Another object of the invention is to provide a vaccine or vaccine composition useful in preventing said diseases.

Still another object of the present invention is to avoid harmful side effects of killed or subunit enterovirus vaccines that induce serotype specific immunity.

Still another object of the present invention is the use of a polio vaccine and/or a non-polio enterovirus vaccine in the manufacture of a vaccine against enterovirus diseases, especially Type I diabetes (IDDM).

The objects of the present invention are fulfilled by providing a method of preventing non-polio enterovirus diseases or of preventing Type 1 diabetes mellitus (IDDM) comprising the administration of an effective amount of oral poliovirus vaccine (OPV) to a human subject.

The invention further encompasses the use of oral poliovirus vaccine (OPV) for the manufacture of a vaccine against non-polio enterovirus diseases, and especially for the manufacture of a vaccine against Type 1 diabetes mellitus (IDDM).

The invention is also directed to a vaccine composition comprising oral poliovirus vaccine (OPV) and a vaccine, which induces serotype specific immunity against non-polio enteroviruses. Preferably the non-polio enterovirus vaccine comprises enterovirus antigens representing diabetogenic enterovirus serotypes or a cocktail thereof.

The invention further relates to the use of a vaccine, which induces serotype specific immunity against one or more serotypes of diabetogenic non-polio enteroviruses selected from the group consisting of coxsackievirus B serotypes 1, 2, 3, 4, 5 and 6, echovirus serotypes 3, 4, 6, 9, 11, 22 and 30, and coxsackievirus A serotypes 9 and 16 for the manufacture of a vaccine against non-polio enterovirus diseases, especially Type 1 diabetes mellitus (IDDM). It also relates to said vaccine and to a method of preventing non-polio enterovirus diseases, especially IDDM, comprising administering an effective amount of said vaccine to a human subject.

The invention further provides a method of preventing non-polio enterovirus diseases, especially Type I diabetes mellitus (IDDM) in the offspring comprising the administration of an effective amount of oral poliovirus vaccine (OPV) to pregnant women, or comprising the administration of an effective amount of oral poliovirus vaccine (OPV) prenatally to the pregnant woman and postnatally to the baby.

A method of preventing non-polio enterovirus diseases, especially IDDM, comprising the administration of repeated doses of an effective amount of oral poliovirus vaccine (OPV) to children is provided.

Finally the invention encompasses a method of avoiding harmful side effects of non-polio enterovirus vaccines, which induce serotype specific immunity against non-polio enteroviruses comprising administering an effective amount of said non-polio enterovirus vaccine simultaneously, before or after administering an effective amount of oral poliovirus vaccine (OPV) to a human subject.

BRIEF DESCRIPTION OF THE DRAWING

FIG. 1 shows the cumulative prevalence of IDDM in cohorts which have never received OPV, or which have received one dose of OPV in childhood or in utero.

DETAILED DESCRIPTION OF THE DRAWINGS

"OPV" is an abbreviation of oral poliovirus vaccine, and means a vaccine that comprises live attenuated polioviruses of one, two or all three of the serotypes or infectious cDNA or RNA thereof. Besides being administered orally OPV may also be given by any other mucosal route like per rectum or intranasally or it may be given parenterally. OPV comprising attenuated viruses of all three serotypes is commercially available and is also called Sabin vaccine.

"IPV" is another commercially available poliovaccine, which comprises killed inactivated polioviruses of all three serotypes. This vaccine is called Salk vaccine.

"IDDM" means insulin-dependent diabetes mellitus, which is the same as Type 1 Diabetes Mellitus or Type 1 Diabetes.

"Non-polio enterovirus diseases" means any disease caused by non-polio enteroviruses e.g. meningitis, paralysis, myocarditis, generalized infections in newborns, hand, foot and mouth-disease, herpangina, pleurodynia, hepatitis, rash, exanthemas, respiratory diseases including pneumonia, dilated cardiomyopathy, atherosclerosis, postviral fatigue syndrome and Type 1 diabetes mellitus.

"An effective amount" of a vaccine is an amount, which is able to elicit a protective immune response in the recipient, either by eliciting neutralizing antibodies or a cell-mediated response, or both.

A vaccine that induces "serotype specific immunity" is the same as a vaccine that induces neutralizing antibodies. Such vaccines may be killed vaccines, subunit vaccines or cDNA or RNA fragment vaccines, wherein the fragment encodes an antigenic part or an inactivated form of the virus.

A "killed vaccine" is the same as an inactivated vaccine i.e. a vaccine comprising viruses treated so that they have lost their infectivity. A "subunit vaccine" comprises only an antigenic part or parts of the viruses, not the whole viruses.

A "diabetogenic enterovirus" is an enterovirus that is associated with the induction of diabetes. These viruses are represented by the group consisting of coxsackievirus B serotypes 1, 2, 3, 4, 5 and 6, echovirus serotypes 3, 4, 6, 9, 11, 22 and 30, and coxsackievirus A serotypes 9 and 16. However, also other serotypes of non-polio enteroviruses might be involved in the induction of diabetes.

Each of all three poliovirus serotypes can cause paralytic disease. Oral poliovirus vaccine used in the present invention may contain only one of them or their different combinations. Preferably it contains a cocktail of all these three serotypes (serotypes 1-3). The vaccine viruses of the OPV used are attenuated polioviruses, the virulence of which has been reduced. This may be carried out by different methods including serial passage of the virus in cell cultures, antigenic modification by chemical treatments, construction of recombinant or chimeric viruses, mutagenization of viral genome, deletion of cer-tain gene regions, selection of temperature sensitive mutants or irradiation. Alternatively, vaccine viruses may be attenuated natural poliovirus isolates or infectious poliovirus cDNA or RNA having reduced capability to cause clinical disease. Typically, the presented immunization regime is based on the use of the commercially available and widely used Sabin oral poliovirus vaccine, which contains all three poliovirus serotypes in each vaccine dose. It is administered orally and replicates in the intestine, but does not cause paralytic polio or other clinical manifestations.

Each immunizing dose of OPV includes infective viruses or infective RNA or cDNA in a titre, which is able to produce infection in humans. This dose would correspond to that which is used in the traditional Sabin-type live oral poliovirus vaccine including a minimum of 105.5-106 TCID50 for poliovirus Type 1, 105 TCID50 for poliovirus type 2 and 105.5-105.8 TCID50 for poliovirus type 3 live attenuated Sabin strains of polioviruses. The dose may also be an-other, if it has been confirmed to be safe and infectious. (TCID=tissue culture infectious dose; TCID50=the dose which infects 50% of the cultures.)

The new non-polio enterovirus vaccines of the present immunization regime may include either whole viruses, the infectivity of which has been inactivated, or sub-unit vaccines containing certain antigenic structures of the virus, or their combination, or fragments of viral RNA or cDNA coding for anti-genic structures of the virus. Inactivated vaccines may be produced by propa-gating the virus in cell cultures and by purifying it from infected cells and culture media by high-speed centrifugation in a density gradient formed by sucrose or other high-density media. Alternatively the virus could be purified by chromatography. The infectivity of the purified viruses is destroyed by inactivating the viruses by chemical treatment (e.g, formalin inactivation like that used to produce IPV), irradiation or heat treatment. Sub-unit vaccines may consist of purified viral proteins or recombinant viral proteins, synthetic peptides corresponding to viral antigenic epitopes or empty viral capsids, which are produced during infection but lack the viral genome. These subunit vaccines can be administered either as such or conjugated to haptens or carriers (e.g. ISCOM particles).

The new non-polio enterovirus vaccines can be given parenterally or by mucosal route like per os, per rectum or intranasally. Each immunizing dose includes viral structures in a titre, which is able to induce proper immune response in humans. This dose would correspond to that used in Salk-type in-activated poliovirus vaccine including 1.8-2 g of viral protein per each dose and 20-40 antigenic D-units of poliovirus type 1, 4-8 antigenic D-units of po-liovirus type 2 and 16-32 antigenic D-units of poliovirus type 3. The dose may also be another, if it has been confirmed to be safe and immunogenic.

In addition to the active ingredients that elicit an immune response, the OPV and the non-polio enterovirus vaccines used in the present invention may comprise pharmaceutically acceptable excipients, carriers, haptens and adjuvants. Excipients, carriers, haptens and adjuvants may include for example phenoxyethanol, magnesium chloride, sucrose, thiomersal, formaldehyde, phenol, antibiotics (preservatives) or aluminium salts, ISCOM particles, carrier proteins (e.g. cholera toxin), liposomes or protein micelles (haptens/adjuvants).

A new regime for the prevention of diseases caused by non-polio enteroviruses is introduced (Table 1).

TABLE 1

Main immunization regime

Action 1. OPV during pregnancy
Given preferentially during the first trimester but may also be given later during pregnancy. May also be given to women who are at fertile age but not pregnant.
Action 2. OPV in childhood
Given at the age of 0, 6, 10, 14 weeks, boosters at older age (e.g. every 5 years).
Action 3. Killed/subunit vaccine
Given at the age of 3, 6 and 12 months, boosters at older age. Can also be given to pregnant mothers.

Actions 1, 2 and 3 can be used separately or in different combinations. The timing of childhood OPV vaccinations in action 2 may vary but the first ones should preferentially be given by the age of 3 months.
Killed or subunit vaccine includes one or more of the following enterovirus serotypes or their antigenic structures: coxsackievirus B serotypes 1, 2, 3, 4, 5 and 6, echovirus serotypes 3, 4, 6, 9, 11, 22 and 30, coxsackievirus A serotypes 9 and 16. It can be given during pregnancy and at varying ages in childhood with booster given later in life. Killed or subunit enterovirus vaccine may be given simultaneously, before or after OPV is given.

Protection against non-polio enteroviruses is induced by extensive immunization by repeated doses of live attenuated oral poliovirus vaccine (OPV). The regime includes prenatal and postnatal OPV vaccinations, which can be used in combination or separately. Prenatal vaccination is carried out by giving OPV to pregnant women in order to protect the child in utero and in infancy (Action 1 in Table 1). This protection is based on anamnestic immune response, which is induced by OPV-vaccination. Anamnestic response is due to the activation of cross-reactive enterovirus specific memory T-cell clones and leads to increases in antibody levels against those enterovirus serotypes to which the mother has been exposed prior to the OPV vaccination. Anamnestic antibody response of the mother protects the child because IgG class maternal antibodies are transferred to the fetus through the placenta and are thus protecting the child until the age of 6-12 months when maternal antibodies disappear from child's circulation.

Postnatal vaccination (Action 2) is carried out like OPV vaccination schedules in general but may be more extensive to get maximal stimulation of cross-reactive T-cell immunity (Table 1). It includes repeated vaccinations, first ones given at birth and during the first weeks of life followed by booster vaccinations in childhood with a few years intervals (like in WHO EPI-program). OPV-vaccination per os induces also strong local immune response in mucosal surfaces, particularly in the gut. This is important because the primary replication site of enteroviruses is gut-associated lymphoid tissue. This local immunity is targeted also to non-polio enteroviruses because of OPV induced cross-reactive T-cell response and induction of local production of interferons.

The Actions 1 and 2 of this regime can be combined with new non-polio enterovirus vaccines, which induce serotype specific immunity to get maximal protective effect against non-polio enteroviruses (Action 3 in Table 1). Serotype specific immunity may be induced by killed enterovirus particles or sub-unit vaccines carrying certain enterovirus structures or peptides. This serotype specific vaccine can be given to pregnant mothers as well as to children as described in Table 1. The serotype specific vaccine preferably includes one or more of the following enterovirus serotypes (coxsackievirus B serotypes 1, 2, 3, 4, 5 and 6, echovirus serotypes 3, 4, 6, 9, 11, 22 and 30, and coxsackievirus A serotypes 9 and 16). This kind of killed or subunit vaccines induce efficient antibody response but the protection is specific for those viruses which are included in the vaccine (protection by neutralizing antibodies is serotype specific). In such combination OPV can be used to give additional protection by cross-reactive T-cell responses against the serotypes which are not included in the killed/subunit vaccine. OPV can also be used to booster the antibody responses which are induced by killed/subunit vaccines. OPV can also be used to direct the immune responses induced by killed/subunit vaccines to Th1-type responses rather than Th2-type responses. Th2-type responses are typically induced by killed/subunit vaccines and can be associated with serious side-effects leading to more severe course of natural infection in vaccinated individuals (like observed in individuals vaccinated by killed RSV or measles vaccines). OPV like other live vaccines induces mainly Th1-type responses leading to cytotoxic T-cell responses and can thus counteract the Th2-type responses induced by killed/subunit vaccines by inducing cross-reactive Th1-type T-cells. To avoid Th2-responses OPV may be given either before, simultaneously with or after the killed/subunit vaccines are given.

Thus, the present regime includes OPV-vaccinations to induce systemic T-cell responses and local mucosal immunity as well as anamnestic antibody responses in pregnant mothers (Actions 1 and 2). OPV vaccinations can be combined with new inactivated or subunit enterovirus vaccines (Action 3). This combination would give maximal preventive effect (neutralizing antibodies induced by killed/subunit vaccines are the first barriers against infections and T-cell immunity induced by OPV helps in the eradication of infection). OPV may also be used in combination with inactivated or subunit vaccines to prime or booster their effect or to prevent possible harmful side-effects caused by Th2-type bias in immune response to enteroviruses which may be caused by inactivated or subunit vaccines.

We have found that there are unexpected side-effects of IPV vaccines, which increase the risk of complications of non-polio enterovirus infections like Type 1 diabetes by directing the immune response against non-polio enteroviruses into the Th2 direction. However, OPV is beneficial, because it decreases the risk of complications of non-polio enterovirus infections and vaccinations of inactivated/subunit non-polio enterovirus vaccines (e.g. against diabetes) by inducing cross-reactive memory T-cells, by directing the immune response to non-polio enteroviruses into the Th1 direction and by inducing local protection in the mucosal tissues.

One advantage of this invention is that it is based on a widely used and very safe vaccine (OPV) but gives a new indication for this vaccine, which has not been previously suggested. The novel aspects are also that the invention utilises strong T-cell responses induced by live OPV vaccine, the cross-reactivity of these responses between different enterovirus serotypes, induction of local immune responses by OPV in mucosal surfaces in pharynx and in gut, vaccination of both pregnant women and children, and optional combination of OPV and new serotype specific killed/subunit vaccines to booster their effect and to avoid their side-effects related to Th2-based responses. An additional novel aspect is that the inactivated/subunit vaccine includes serotypes, which are the most important in the pathogenesis of severe non-polio enterovirus diseases including Type 1 diabetes.

This vaccination regime can be used in the whole population or in specific high-risk groups such as children with genetic risk alleles for Type 1 diabetes, children with diabetes in first-degree relatives or children positive for diabetes-related autoantibodies.

This vaccination regime is the only possibility which is currently available for the prevention of non-polio enterovirus diseases in man. It can be implemented into clinical work immediately as it is based on currently widely used and well-tolerated vaccine (OPV). It can be coupled with inactivated or subunit enterovirus vaccines to increase their preventive effect and to avoid their side-effects.

Figure 1:
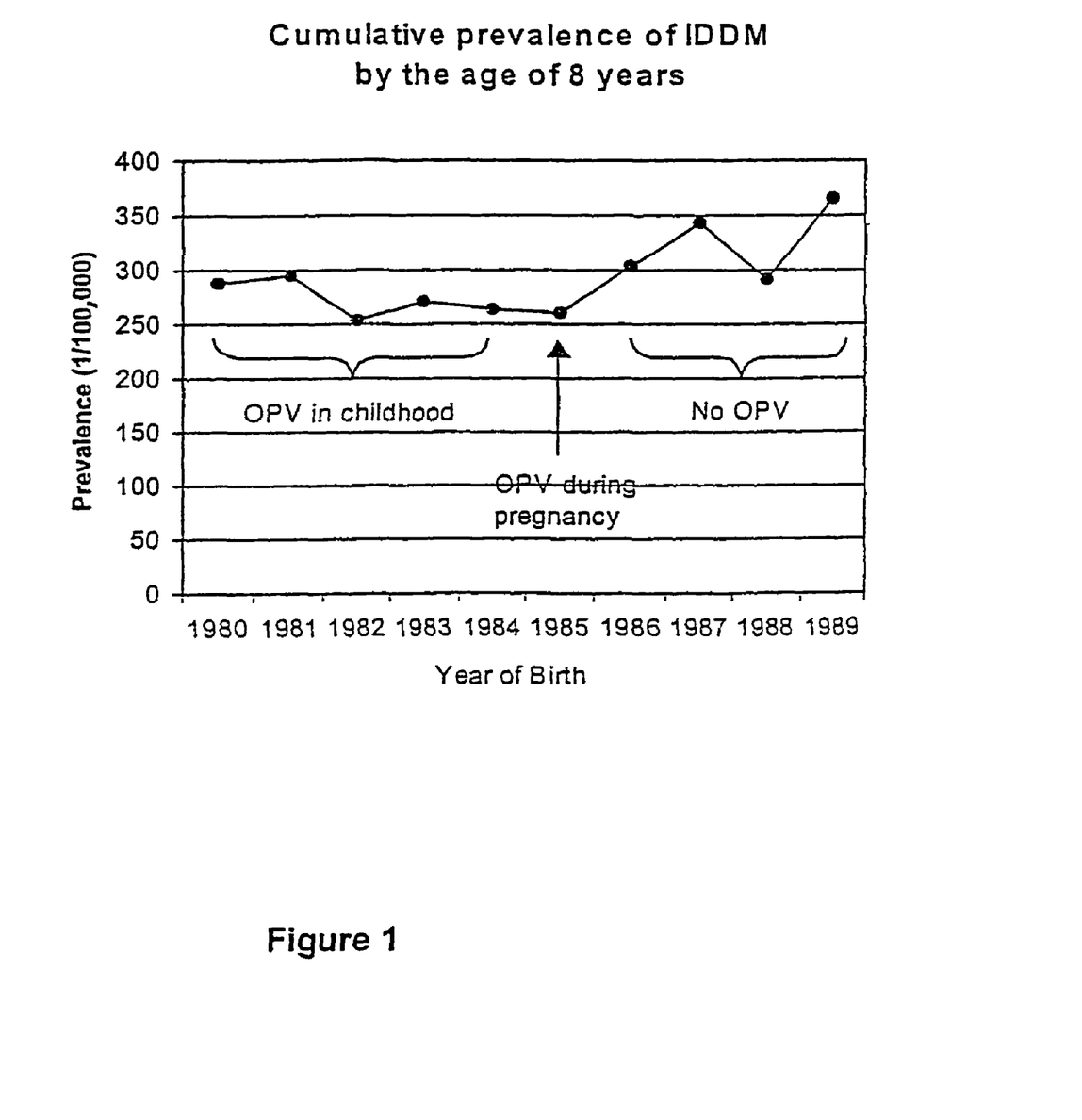

In Finland practically the whole population was vaccinated by one dose of OPV in February-March in the year 1985 to eradicate the last polioepidemic (Hovi et al., 1986; Harjulehto-Mervaala et al., 1994). This provides an excellent possibility to analyze possible effects of OPV vaccination on the risk of type 1 diabetes because IPV has been used as the only poliovirus vaccine for decades and has also been used after the epidemic. OPV vaccination was also given to pregnant women (Harjulehto-Mervaala et al., 1993). We have analysed the cumulative prevalence of type 1 diabetes in birth cohorts which have received OPV vaccination in the year 1985 either in childhood or in utero and compared that to cumulative prevalence in birth cohorts who had never received OPV (FIG. 1). The FIGURE shows the cumulative prevalence of Type 1 diabetes (IDDM) per 100,000 children by the age of 8 years in Finland in birth cohorts which have either never received oral poliovirus vaccine (OPV) or have been vaccinated by one dose of OPV in childhood or in utero during the mass-vaccination campaign in 1985. The cumulative prevalence of type 1 diabetes was significantly lower in OPV-vaccinated cohorts compared to unvaccinated cohorts: The average prevalence in OPV vaccinated cohorts born in the years 1980-1985 was 272 compared to 326 in unvaccinated cohorts born in 1986-1989 ($p<0.01$ in student's t-test). The prevalence of diabetes was also low in children whose mother had been vaccinated during pregnancy (261 per 100,000; FIG. 1). These findings indicate that both Actions 1 and 2 in the proposed immunisation regime (see Table 1) have a protective effect against Type 1 diabetes.

We have also found that incidence of Type 1 diabetes correlates with the type of poliovirus vaccine used in different countries. This correlation is not absolute but there is a general tendency to a lower incidence of Type 1 diabetes in countries where OPV is used compared to countries where inactivated (killed) poliovirus vaccine (IPV) is used. In Finland the incidence of Type 1 diabetes is the highest in the world, and Finland is also one of the very few countries where IPV has been used as the only poliovirus vaccine for several decades (except in the year 1985 as mentioned before).

A possible role of different poliovaccination regimes as a cause of the international differences in the incidence of Type 1 diabetes is also supported by our findings in Estonian and Finnish children. In Estonia, where the incidence of Type 1 diabetes is one third of that in the neighbouring Finland, OPV is used as the only poliovirus vaccine in contrast to Finland where IPV is used. We analysed T-cell proliferation responses to tetanus toxoid, poliovirus type 1, coxsackievirus B4 (CBV4) and adenovirus antigens in 9-months-old in-fants in both countries. The responses to poliovirus and CBV4 were signifi-cantly higher in Estonian than in Finnish children ($p<0.05$) while responses to other antigens did not differ between the groups. Neutralizing antibodies against CBV group enteroviruses did not differ between the groups suggesting that the observed difference in T-cell responses was not due to different exposure of infants to enteroviruses in the two countries. Accordingly, the higher T-cell response to purified CBV4 virus in Estonian children probably reflects cross-reactivity of T-cells primed by previous OPV vaccinations. In Finland, the IPV vaccine is used which does not induce as high T-cell responses as OPV and which is also given at older age than OPV in Estonia (Estonian children had received three doses of OPV compared to one dose of IPV in Finnish children by the age of 9 months). This suggests that the OPV vaccination schedule in Estonia induces stronger cross-reactive immune response to non-polio enteroviruses than the IPV vaccination schedule used in Finland. This indicates that Action 2 in our immunisation immunization regime (see Table 1) has a protective effect against Type 1 diabetes.

In the Finnish Diabetes Prediction and Prevention study (DIPP) we have analysed the frequency and serotype of enterovirus infections in 21 infants who have been followed from the birth and who have manifested with clinical Type 1 diabetes or turned positive for diabetes-related autoantibodies as a marker of subclinical beta-cell damage. Enterovirus infections were more frequent in these children than in 104 control children matched for the time of birth, gender and HLA-risk alleles for Type 1 diabetes ($p<0.03$). This difference was particularly clear in infections which occurred 0-6 months before autoantibodies appeared: 57% of autoantibody positive subjects had an enterovirus infection during that period compared to 31% of control subjects of the same age (OR 3.7, 95% Cl 1.2-11.4) (unpublished observation). During this period 29% of autoantibody positive children were positive for enterovirus RNA in serum compared to 6% of control subjects (OR 8.4, 95% Cl 1.7-40.2). The results suggest that enterovirus infections are important risk factors for Type 1 diabetes and able to initiate the beta-cell damaging process in genetically susceptible individuals. The average age of the infants at the appearance of autoantibodies was 9 months suggesting that diabetogenic enterovirus infections may occur already during the very first months of life.

The serotype of enterovirus infections related to induction of autoantibodies or manifestation of clinical diabetes has been analysed in the DIPP study and in the previous Childhood Diabetes in Finland (DiMe) study. These serotypes are included in the killed/subunit vaccine in the present immunisation regime (Action 3 in Table 1).

OPV vaccinations can be combined not only with serotype specific vaccines but also with passive immunization regimes against enteroviruses. This kind of passive immunization may include e.g. immunoglobulins which contain enterovirus specific antibodies and which are given intravenously or orally.

Example 1

We have analysed the effect of OPV vaccination on the course of subsequent coxsackievirus B3 (CBV3) infection in mice. In these studies we used a transgenic BALB/c strain which expresses human poliovirus receptor and can therefore be infected by human polioviruses (Horie et al., 1.994).

Transgenic BALB/c mice were first immunized by live poliovirus vaccine (Sabin strain of poliovirus type 1) or inactivated poliovirus vaccine IPV, and later challenged to a pancreas-tropic strain of coxsackievirus B3 (Nancy strain). (IPV was the commercially available poliovirus vaccine Novum purchased by National Public Health Institute of Holland). Two doses of live poliovirus vaccine strain type 1 (Sabin) were given intramuscularly with two weeks intervals (108 $TCID_{50}$/mouse, first injection at the age of 8 weeks). Two doses of killed poliovirus vaccine were given intramuscularly in the same way (0.1 μg per mouse). Two weeks after the last poliovirus injection the mice were infected by coxsackievirus B3. T-cell proliferation responses were analysed two weeks after the coxsackievirus B3 challenge using standard blast-transformation test and highly purified viruses as antigens. The T-cell responses are expressed as specific counts (mean cpm), and the results are shown in Table 2.

TABLE 2

Effect of previous poliovirus immunization on T-cell proliferation responses during subsequent coxsackievirus B3 infection in transgenic mice expressing human poliovirus receptor.

| Virus antigen | Proliferation response in different immunization groups (mean cpm values) | | |
|---|---|---|---|
| | PBS (N = 5) | IPV (N = 5) | Sabin (N = 5) |
| Coxsackievirus B3 | 1444 | 3669 | 6485 |
| Poliovirus type 1 | 1927 | 4898 | 6738 |

Grading of coxsackievirus B3 induced pancreatitis and myocarditis as well as the detection of viremia was done two weeks after the coxsackievirus B3 challenge. The presence of viremia was analysed at the same time by detecting viral RNA in serum using a sensitive RT-PCR method. The results are shown in Table 3.

TABLE 3

Effect of previous poliovirus immunization on the pathogenesis of subsequent coxsackievirus B3 infection in transgenic mice expressing human poliovirus receptor.

| | | Immunisation group | | |
|---|---|---|---|---|
| | | PBS (N = 5) | IPV (N = 5) | Sabin (N = 5) |
| Pancreatitis | +++ | 2 | 0 | 4 |
| | ++ | 3 | 2 | 1 |
| | + | 0 | 1 | 0 |
| | − | 0 | 2 | 0 |
| Myocarditis | +++ | 0 | 0 | 0 |
| | ++ | 0 | 0 | 1 |
| | + | 3 | 2 | 3 |
| | − | 2 | 3 | 1 |
| Viremia | + | 2 | 3 | 1 |
| | − | 3 | 2 | 4 |

In the experiments live poliovirus vaccine (Sabin strain) increased in vitro T-cell proliferation responses during subsequent coxsackievirus B3 infection. This increase was observed in proliferation responses against both purified coxsackievirus B3 and poliovirus type 1 (Table 2). This suggests that previous live poliovirus vaccination can augment cellular immune responses during subsequent non-polio enterovirus infection. Previous IPV vaccination also enhanced T-cell responses during subsequent coxsackievirus B3 infection but the effect was weaker that that of live vaccine (Table 2).

Previous immunization with live poliovirus vaccine (poliovirus type 1, Sabin vaccine strain) increased T-cell infiltration in the pancreas during subsequent infection with a pancreas-tropic strain of coxsackievirus B3 (Table 3). In contrast, previous IPV vaccination was associated with weak T-cell infiltration in the pancreas as compared to that observed after live poliovirus vaccine or that in control mice. These results suggest that live poliovirus vaccination augment in vivo T-cell responses during subsequent non-polio enterovirus infections while killed poliovirus vaccine may have an opposite effect.

There was also a tendency of a low frequency of viremia in mice previously immunized with live poliovirus. This suggests that live poliovirus vaccination facilitates the eradication of subsequent non-polio enterovirus infections.

In another experiment it was found that altogether 9 (92%) out of the twelve poliovaccinated mice had T-cell infiltration in the heart compared to 7 (53%) of the fifteen unvaccinated mice. This suggests that prior challenge by live poliovirus exaggerates T-cell response during-CBV3 infection in vivo.

Example 2

We have produced and tested formalin-inactivated coxsackievirus B vaccines in mice. These vaccines were produced by inactivating sucrose gradient purified viruses by 14 days incubation at +37° C. in 0.01% formalin in PBS.

Mean IgG1 antibody levels against purified coxsackievirus B3 were determined in Balb/c mice immunized by 3 repeated intramuscular injections with formalin-inactivated coxsackievirus B3 vaccine or phosphate buffered saline (PBS). Injections were given with two weeks intervals (first one at 8 weeks of age) and antibodies were measured at 2 weeks after the last vaccination. Antibody levels are expressed as $OD_{492}$ values in EIA (Table 4).

TABLE 4

Antibody levels induced by inactivated coxsackievirus B3 vaccine in mice

| | Immunization group | |
|---|---|---|
| Serum dilution | PBS (N = 5) | Coxsackievirus B3 vaccine (N = 5) |
| 1/1600 | 0.12 | 0.95 |
| 1/6400 | 0.13 | 0.47 |
| 1/25600 | 0.14 | 0.28 |

Presence of viremia (virus in serum) was determined in BALB/c mice immunized with three repeated intramuscular injections with formalin-inactivated coxsackievirus B3 vaccine or with phosphate buffered saline (PBS) and subsequently infected with a pancreas-tropic strain of coxsackievirus B3 (Nancy strain, 106 TCID50/mouse). Immunizations were done with two weeks intervals (first one at 8 weeks of age) and mice were infected 2 weeks after the last injection. The presence of virus in serum (viremia) was analysed three days after the infection using the end-point dilution assay of infectivity. End-point dilution of infectivity in LLC-cell cultures is presented in Table 5.

TABLE 5

Protection against viremia by immunisation with an inactivated coxsackievirus B3 vaccine

| | Immunisation group | |
|---|---|---|
| Mice | PBS | Coxsackievirus B3 vaccine |
| 1. | $10^{-3}$ | ND |
| 2. | $10^{-3}$ | ND |
| 3. | $10^{-1}$ | ND |
| 4. | $10^{-4}$ | ND |
| 5. | $10^{-1}$ | ND |

ND: Not detectable (titre $<10^{-1}$)

As shown in Table 4 immunization with inactivated coxsackievirus B3 vaccine induced high levels of antibodies as measured against purified coxsackievirus B3 in ETA test. We also found that vaccination completely protected the mice against infection by a pancreas-tropic strain of coxsackievirus B3. Virus could not be detected in the serum in any of the vaccinated animals while all control mice were positive for the virus (Table 5). This vaccine also protected the mice from virus-induced pancreatitis: None of the vaccinated animals had T-cell infiltration in the pancreas while all control mice had a very strong inflam-matory response.

These results suggest that inactivated non-polio enterovirus vaccines are effective in the protection against non-polio enterovirus infections. This protection is probably mediated by neutralizing antibodies induced by the vaccine.

Example 3

SJL/J mice were first immunized either with formalin-inactivated poliovirus vaccine (IPV; 0.1 g/mouse), or with saline (PBS). After 14 days the mice were infected with coxsackievirus B3 intramuscularly (106 TCID50/mouse). Histopathology of the pancreas was analysed 14 days after the infection. The results are shown in Table 6.

TABLE 6

Inflammation reaction (T-cell infiltration) in the pancreas of SJL/J mice infected intramuscularly with a pancreas tropic strain of coxsackievirus B3 (Nancy strain).

| | Vaccine | |
|---|---|---|
| Pancreatic inflammation | PBS (N = 5) | IPV (N = 5) |
| Strong | 1 | 4 |
| Moderate | 2 | 1 |
| Not detected | 2 | 0 |

Our observations indicate that IPV increases the severity of non-polio enterovirus infections. We have found that mice, which have first been immunized by IPV and later infected with a non-polio enterovirus, namely a pancreas tropic Nancy strain of coxsackievirus B3, had more severe pancreatitis than mice which had not previously been immunized with IPV (Table 6).

Mean IgG1 antibody levels against purified coxsackievirus B3 were determined in BALB/c mice immunized with three intramuscular injections with formalin-inactivated poliovirus vaccine (IPV; 0.1 g per mouse) or with phosphate buffered saline (PBS) and subsequently infected with a pancreas-tropic strain of coxsackivirus B3 (Nancy strain, 106 TCID50/ mouse). Immunizations were done with two weeks intervals (first one at 8 weeks of age), mice were infected 2 weeks after the last injection and antibodies were measured 2 weeks after the infection. Antibody levels are expressed as mean OD492 values in EIA (Table 7). IPV was the commercially available poliovirus vaccine Novum pur-chased by National Public Health Institute of Holland.

TABLE 7

Effect of immunization with inactivated poliovirus vaccine on antibody response during subsequent coxsackievirus B3 infection

| | Immunization group | |
|---|---|---|
| Serum dilution | PBS (N = 5) | IPV (N = 5) |
| 1/1600 | 0.50 | 0.37 |
| 1/6400 | 0.36 | 0.11 |
| 1/25600 | 0.32 | 0.08 |

IPV vaccination was associated with abnormally low antibody response during subsequent coxsackievirus B3 infection in BALB/c mice (Table 7). This suggests that immunization with killed poliovirus vaccine may weaken antibody responses during subsequent non-polio enterovirus infections in vivo. This, in turn, may increase the severity of non-polio enterovirus infections.

We assume that the harmful effect of IPV is due to its ability to induce Th2-type immune responses. It has been shown previously that inactivated vaccines induce mainly Th2 type responses and that this kind of Th2 bias may increase the severity of natural infections (like in the case of inactivated respiratory syncytial virus and measles vaccine). This harmful effect is manifested particularly in infections caused by other serotypes than that used in the vaccine while infections by the same serotype as that used in the vaccine are totally protected by the vaccine (as shown in our mice experiments described in Table 5). This serotype-specific protection is based on vaccine-induced neutralizing antibodies. Thus IPV vaccination in childhood primes poliovirus specific immune response towards Th2 direction, which imprints T-cell memory in later enterovirus infections. Due to cross-reactive T-cells this Th2-bias will spread to immune responses against non-polio enteroviruses thus increasing the severity of non-polio enterovirus infections and the risk of their complications like Type 1 diabetes.

In contrast to the harmful effect of IPV on immune protection against non-polio enterovirus infections, OPV has a beneficial effect. As a live vaccine OPV induces stronger T-cell responses than IPV. In addition, this immune response is more balanced resembling that observed in natural enterovirus infections including both Th1- and Th2-type immune responses. This response is targeted to both structural and non-structural virus proteins, while IPV induces only response to structural virus proteins. By inducing strong T-cell responses OPV activates also memory T-cells, which can cross-react between polio and non-polio enteroviruses and booster both T-cell and antibody responses against non-polio enteroviruses. By this mechanism, OPV facilitates the clearance of non-polio enterovirus infections thus preventing from their complications. Thus, the risk of complications of non-polio enterovirus infections (like Type 1 diabetes) can be prevented by OPV.

In addition to the natural non-polio enterovirus infections, OPV can also be used to convert immune responses, which have been induced by inactivated or sub-unit enterovirus vaccines from Th2-type responses to Th1 direction. In this way OPV can be used to protect from the Th2-dependent side effects of inactivated or sub-unit non-polio enterovirus vaccines. This kind of side effects have been described in the context of the use of inactivated respiratory synsytial virus and measles virus vaccines and they include abnormal course of infections, increased severity of the infection, increased risk of complications of the infection and possible development of allergies and asthma.

Accordingly, OPV can be used to dictate the immune response induced by inactivated or subunit enterovirus vaccines to Th1-type responses thus protecting against the side-effects of such vaccines. In contrast, IPV may have an opposite effect increasing the risk of complications of non-polio enterovirus infections by dictating the immune response to Th2 direction.

An additional advantage of OPV over IPV is that as a live virus it induces production of interferon-alpha. It is induced only during virus infections and is the most potent antiviral cytokine (part of the innate immunity). It specifically protects against virus infections and provides protection before the antigen specific immune responses are induced. As a live virus OPV induces interferon-alpha and this induction happens both in mucosal surfaces and systemically. Vaccine viruses replicate in the gut for several weeks, which means that local production of interferon-alpha persists for prolonged periods in children repeatedly vaccinated by OPV. This will augment to the protective effect of OPV against non-polio enterovirus infections.

REFERENCES

Beck M A, Tracy S M. Evidence for group specific enterovirus antigens recognized by human T-cells. J Clin Microbiol 28: 1822-1827, 1990.

Fohlman J, Pauksen K, Morein B, Bjare U, Ilback N G, Friman G. High yield production of an inactivated coxsackie B3 adjuvant vaccine with protective effect against experimental myocarditis. Scand J Infect Dis Suppl 88:103-8, 1993.

Fohlman J, Ilback N G, Friman G. Morein B. Vaccination of Balb/c mice against enteroviral mediated myocarditis. Vaccine 8:381-4, 1990.

Fulginiti V A, Eller J J, Downie A W, Kempe C H. Altered reactivity to measles virus. Atypical measles in children previously immunized with inactivated measles virus vaccines. JAMA 202: 1075-1080, 1967.

Graham S, Wang E CY, Jenkins O, Borysiewicz L K. Analysis of the human T-cell response to picornaviruses: identification of T-cell epitopes in poliovirus. J Virol 67: 1627-1637, 1993.

Harjulehto-Mervaala T, Aro T, Hiilesmaa V K, Hovi T, Saxen H, Saxen L. Oral polio vaccination during pregnancy: lack of impact on fetal development and perinatal outcome. Clin Infect Dis 18:414-20, 1994.

Harjulehto-Mervaala T, Aro T, Hiilesmaa V K, Saxen H, Hovi T, Saxen L. Oral polio vaccination during pregnancy: no increase in the occurrence of congenital malformations. Am J Epidemiol 138:407-14, 1993.

Harris R W, Isacson P, Karzon D T. Vaccine-induced hypersensitivity: reactions to live measles and mumps vaccine in prior recipients of inactivated measles vaccine. J Pediatr 74: 552-63, 1969.

Horie H, Koike S, Kurata T, et al., Transgenic mice carrying human poliovirus receptor: New animal model for study of poliovirus neurovirulence. J Virol 68: 681-688, 1994.

Hovi T, Cantell K, Huovilainen A, Kinnunen E, Kuronen T, Lapinleimu K, Poyry T, Roivainen M, Salama N, Stenvik M, et al. Outbreak of paralytic poliomyelitis in Finland: widespread circulation of antigenically altered poliovirus type 3 in a vaccinated population. Lancet 1:1427-32, 1986.

Juhela S, Hyöty H, Lönnrot M, Roivainen M, Simell O, Ilonen J. Enterovirus infections and enterovirus specific T-cell responses in infancy. J Med Virol 54: 226-232, 1998.

Kapikian A Z, Mitchell R H, Chanock R M, Shvedoff R A, Stewart C E. An epidemiological study of altered clinical reactivity to respiratory syncytial (RS) virus infection in children previously vaccinated with an inactivated RS virus vaccine. Am J Epidemiol 89: 405-421, 1969.

See D M, Tilles J G. Occurrence of coxsackievirus hepatitis in baby rabbits and protection by a formalin-inactivated polyvalent vaccine. Proc Soc Exp Biol Med 216:52-6, 1997

See D M, Tilles J G. Efficacy of a polyvalent inactivated-virus vaccine in protecting mice from infection with clinical strains of group B coxsackieviruses. Scand J Infect Dis 26:739-47, 1994

We claim:

1. A method for reducing risk of contracting Type 1 Diabetes mellitus (IDDM) comprising the steps of selecting from a population as a whole a child from a high risk group consisting of children with genetic risk alleles for Type I Diabetes Mellitus (IDDM), children having first degree relatives with diabetes, and children tested positive for diabetes-related autoantibodies, and administering an inactivated or subunit, diabetogenic non-polio enterovirus vaccine that induces neutralizing antibodies to at least one diabetogenic non-polio enterovirus to reduce his or her risk of contracting IDDM, wherein the at least one diabetogenic non-polio enterovirus is selected from the group consisting of coxsackievirus B serotypes 1, 2, 3, 4, 5 and 6, echovirus serotypes 3, 4, 6, 9, 11, 22 and 30, and coxsackievirus A serotypes 9 and 16.

2. The method according to claim 1, wherein said at least one diabetogenic non-polio enterovirus comprises coxsackievirus B serotype 3.

3. The method according to claim 2, wherein said at least one diabetogenic non-polio enterovirus further comprises one or more serotypes of diabetogenic non-polio enteroviruses selected from the group consisting of coxsackievirus B serotypes 1, 2, 4, 5 and 6, echovirus serotypes 3, 4, 6, 9, 11, 22 and 30, and coxsackievirus A serotypes 9 and 16.

4. The method according to claim 1, wherein the child has genetic risk alleles for IDDM.

5. The method according to claim 1, wherein the child has first-degree relatives with diabetes.

6. The method according to claim 1, wherein the child has tested positive for diabetes-related autoantibodies.

7. A method for reducing risk of contracting Type 1 Diabetes mellitus (IDDM) comprising the steps of selecting from a population as a whole a child from a high risk group consisting of children with genetic risk alleles for Type I Diabetes Mellitus (IDDM), children having first degree relatives with diabetes, and children tested positive for diabetes-related autoantibodies, and administering an inactivated or subunit, diabetogenic non-polio enterovirus vaccine that induces neutralizing antibodies to at least one diabetogenic non-polio enterovirus to reduce his or her risk of contracting IDDM, wherein the at least one diabetogenic non-polio enterovirus is selected from the group consisting of coxsackievirus B serotypes 1, 2 and 6, echovirus serotypes 3, 4, 6, 9, 11, 22 and 30, and coxsackievirus A serotypes 9 and 16.

8. The method according to claim 7, wherein the child has genetic risk alleles for IDDM.

9. The method according to claim 7, wherein the child has first-degree relatives with diabetes.

10. The method according to claim 7, wherein the child has tested positive for diabetes-related autoantibodies.

* * * * *